United States Patent [19]
Wagner

[11] 3,968,104
[45] July 6, 1976

[54] EXTREMELY LOW VISCOSITY ADDUCTS OF LACTAMS WITH ALCOHOLS

[75] Inventor: Kuno Wagner, Leverkusen-Steinbuechel, Germany

[73] Assignee: Bayer Aktiengesellschaft, Leverkusen, Germany

[22] Filed: Nov. 14, 1973

[21] Appl. No.: 415,892

Related U.S. Application Data

[63] Continuation-in-part of Ser. No. 207,562, Dec. 13, 1971, abandoned.

[30] Foreign Application Priority Data
Dec. 17, 1970 Germany............................ 2062288

[52] U.S. Cl. ............... 260/239.3 R; 260/326.5 FL; 260/239 A; 260/293.86; 260/326.5 FN; 260/251 R; 232/364
[51] Int. Cl.² ........................................ C07D 223/10
[58] Field of Search ............... 260/239.3 R, 293.86, 260/326.5 FL, 326.5 FN

[56] References Cited
OTHER PUBLICATIONS

Chemical Abstracts, vol. 68 (1968) Item 104540w, abstracting Aarna et al. in "Eesti NSV Tead. Akad. Toim., Keem., Geol." vol. 16, No. 4, pp. 300–306 (1967) (Aarna et al. I).
Chemical Abstracts, vol. 71 (1969) Item 49439e, abstracting Aarna in "Suom., Kemistilehti B" 1969, vol. 42, No. 4, pp. 217–120 (Aarna et al. II).
Chemical Abstracts, vol. 73 (1970) Item 76347w, abstracting Aarna et al. in "Eesti NSV Tead. Akad. Tiom., Keam., Geol." (1970) vol. 19, No. 2, pp. 121–127 (Aarna et al. III).
Chemical Abstracts, vol. 57 (1962) Col. 16550, abstracting Burmistrov et al. in "Tr. Dnepropetr. Khim.-Teknnol. Inst." (1959) Pt. 1, No. 12, pp. 153–157.

*Primary Examiner*—Henry R. Jiles
*Assistant Examiner*—Robert T. Bond
*Attorney, Agent, or Firm*—Burgess, Dinklage & Sprung

[57] ABSTRACT

Adducts useful as solvents are prepared from lactams and an aliphatic, cycloaliphatic or araliphatic alcohol or thioalcohol. Solutions of the adducts in the lactam, alcohol or thioalcohol are also disclosed as well as a process for preparing the adducts and solutions thereof.

8 Claims, No Drawings

EXTREMELY LOW VISCOSITY ADDUCTS OF LACTAMS WITH ALCOHOLS

RELATED APPLICATIONS

This application is a continuation-in-part of copending application Ser. No. 207,562 filed Dec. 13, 1971, now abandoned.

BACKGROUND

This invention relates to extremely low viscosity adducts of lactams with monofunctional or polyfunctional aliphatic, cycloaliphatic or araliphatic alcohols and mercaptans, to a process for their production and to the use of this new class of compounds as, for example, highly active solvents for compounds that are difficult to dissolve.

The new adducts contain 1 mol of such monofunctional or polyfunctional alcohol or mercaptan per mol of lactam.

It has already been proposed to use molten $\epsilon$-caprolactam (70°C) as a solvent for substantially insoluble, relatively high molecular weight substances, for example polymethylene thioureas, optionally in conjunction with inert organic solvents free from hydroxyl groups, such as aromatic hydrocarbons, acetone, ethers, esters, tetrahydrofuran and aliphatic halohydrocarbons as solvents (H. Staudinger and K. Wagner, German Pat. No. 910,336). Disadvantages of this solvent, or of the aforementioned mixtures, include the relatively high melting point of $\epsilon$-caprolactam, and the very marked tendency of caprolactam to crystallise at temperatures below 70°C with the result that it is impossible to prepare solutions which are storage-stable, especially at room temperature and at temperatures below room temperature.

SUMMARY

It has now surprisingly been found that extremely low viscosity adducts are obtained by reacting lactams corresponding to the general formula:

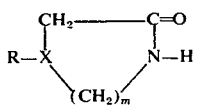

in which
  X represents a CH group and
  R represents hydrogen, and
  m is an integer from 0 to 9; or
  X represents a nitrogen atom,
  R represents an alkyl radical, a cycloaliphatic radical, an araliphatic radical or a pyridyl radical optionally substituted by lower alkyl radicals, and
  m is the number 3,
with an aliphatic, cycloaliphatic or araliphatic alcohol and/or thioalcohol so that from 0.3 to 4 mols of a monofunctional or polyfunctional alcohol or thioalcohol are used per mol of the lactam and/or azalactam. When polyfunctional components are used, the surplus OH— or SH group may also form an adduct with a further mol of lactam.

It is, of course, possible to form a solution of the new adduct in excess lactam, alcohol or thioalcohol.

The quantity in which the alcohol or thioalcohol is used is preferably such that there are from 1.0 to 3 mols, most preferably from 1.2 to 2.0 mols, available per mol of lactam.

The process of the invention is carried out at a temperature of from room temperature to 150°C, preferably at a temperature of from 40° to 100°C, most preferably at a temperature of from 50° to 80°C.

DESCRIPTION

Alcohols and thioalcohols used for the process according to the invention can be characterized by the general formula:

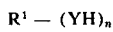

in which
  $R^1$ represents an n-valent optionally substituted linear or branched aliphatic radical containing 1 to 40, preferably 1 to 18, most preferably 1 to 4, carbon atoms which may optionally also contain up to 3 double bonds or one triple bond, and the aliphatic radical can also contain chain members such as oxygen, sulphur, nitrogen, —O—CO—, —NH—COO, —NH—CO— or an NH—CO—NH— group; the expression "aliphatic radicals" also covers cycloaliphatic radicals containing 3 to 12, preferably 5 or 6 carbon atoms, in the ring system,
  $R^1$ can also represent an optionally substituted araliphatic radical, in which the aliphatic chain contains 1 to 4, preferably 1 or 2, carbon atoms and the aromatic radical, in addition to the naphthalene radical, is preferably a benzene radical,
  Y represents oxygen or sulphur,
  n is an integer from 1 to 4, preferably from 1 to 3, most preferably 1 or 2, when Y represents oxygen, or
  n is an integer from 1 to 4, preferably 1 or 2, when Y represents sulphur.

The following are examples of substituents on the aliphatic radical:
Halogens (preferably fluorine, chlorine or bromine), $NO_2$, $NH_2$, $N(R^2)_2$, in which the radicals $R^2$ are preferably methyl, ethyl or cyclohexyl radicals, although one of the radicals $R^2$ can also represent hydrogen or the phenyl radical, CN, CO, —NH—NH$_2$, —CONH$_2$, lower O-alkyl and S-alkyl radicals, oxirane radicals, cyclic acetal groups, especially of formaldehyde, acetaldehyde and of acrolein and an alkoxymethylene group (containing 1 to 4 carbon atoms).

Substituents on the araliphatic radical include: $NO_2$, halogens (preferably fluorine, chlorine or bromine), lower alkyl, O-alkyl, S-alkyl or dialkylamino groups (each with 1 to 4 carbon atoms per alkyl group).

The following lactams are preferably used for the process according to the invention:
$\epsilon$-caprolactam, 1-N-methyl hexahydro-1,4-diazepin-3-one and, optionally, mixtures of the aforementioned lactams with dodecalactam, butyrolactam and valerolactam. The last two lactams can also be employed in pure form.

Aliphatic alcohols preferably used in the process according to the invention include methanol, ethanol, propanol, n-butanol, isopropanol, t-butanol, cyclohexanol, allyl alcohol, glycol monomethyl ether, benzyl alcohol, chlorinated alcohols such as chloroethyl alcohol, fluoroethanol, trichloro- and trifluoro-ethanol, $\beta$-hydroxypropyl ester of $C_{1-4}$ carboxylic acids, furfuryl alcohol and tetrahydrofurfuryl alcohol.

Preferred mercaptans include n-butyl mercaptan, dodecyl mercaptan, mercaptoethanol.

Surprisingly, it is also possible to use as monofunctional alcohols in the process according to the invention hemi-acetals of the aforementioned organic hydroxyl compounds and mercapto compounds, preferably of formaldehyde and chloral, for example compounds of the type:

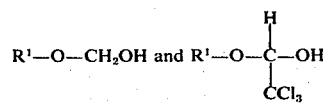

It must be regarded as particularly remarkable because cyclic amides (lactams) which are not substituted on the nitrogen atom, like ε-caprolactam, readily form N-methylol compounds.

Particularly preferred polyfunctional alcohols for the formation of adducts especially with butyrolactam, valerolactam and 1-N-alkyl hexahydro-1,4-diazepin 3-one and especially -caprolactam are the following polyols:

Ethylene glycol, diethylene glycol, thiodiglycol, the isomeric propane diols, di- and tri-propylene glycol, glycerin, trimethylol propane, hexane-1,6-diol and isomers of hexane diol, hexahydroquinone (quinitol), 1,4-bis-hydroxymethyl cyclohexane, terpin hydrate, mono-, di-, tri- and tetramethylol cyclohexanone, anhydroenneaheptitol, phthalic acid and terephathalic acid diglycol esters, and methylene glycol, and all mono- or bis-hemiacetals of formaldehyde and chloral and the aforementioned polyfunctional aliphatic and cycloaliphatic polyhydroxyl compounds also N-methyldiethanolamine, bis-hydroxyethyl cyclohexylamine, and bis-hydroxyethyl stearylamine.

Advantageous adduct formers from the group of organic compounds containing N-hydroxymethyl groups also include N-methylol derivatives of valerolcatam and butyrolactam, those of the azalactams and of N-butylethylurethane, of N-methylol benzamide and N-hydroxymethyl naphthalimide which form storable, liquid adducts with ε-caprolactam, for example, without any methylene-bis-lactams being formed.

From the group of monohydric alcohols containing amino groups and amido groups, the following are preferably used for forming the addition compounds:

Ethanolamine, N-methylethanolamine, cyclohexyl ethanolamine, oxethylated benzamide, hydroxymethyl acetamide, hydroxyethyl carbamic acid butyl ester, N,N-dimethylethanolamine, N,N-diethylethanolamine and hydrazinoethanol.

Among the monofunctional alcohols, the following are also of particular interest:

Primary and secondary alcohols whose molecules contain cyclic acetal groups of formaldehyde, acetaldehyde or acrolein, and alcohols with carbonyl or oxirane groups in the molecule of the kind listed in Table I below.

| No. | Alcohol Component | Lactam Component | Molar ratio |
|---|---|---|---|
| 1 | (glycidol/glyceryl formal structure with CH₂—CH—CH₂OH, O, CH₂, O) | caprolactam ((CH₂)₅, C=O, NH) | 1:1 |
| 2 | (1,3-dioxane with OH: CH₂, H, CH₂, O, O, CH₂) | caprolactam ((CH₂)₅, C=O, NH) | 1:1 |
| 3 | C₂H₅—C(CH₂—O / HOH₂C \ CH₂—O)CH₂ | CH₃—N—CH₂, C=O, (CH₂)₃—NH | 1:1 |
| 4 | C₂H₅—C(CH₂—O / HOH₂C \ CH₂—O)CH₂ | CH₃—N—CH₂, C=O, (CH₂)₃—NH | 1:1 |
| 5 | C₂H₅—C(CH₂—O / HOH₂C \ CH₂—O)CH—CH=CH₂ | (CH₂)₅, C=O, NH | 1:1 |
| 6 | CH₂—CH—CH₂OH (with O bridge) | (CH₂)₃—NH, C=O | 1:1 |
| 7 | C₂H₅—C(CH₂—O / HOH₂C \ CH₂—O)C=O | (CH₂)₃—NH, C=O | 1:1 |

The new adducts whichh can be obtained by the process according to the invention are extremely low viscosity, generally crystal-clear compounds which have a viscosity of from 2 to 160, preferably from 3 to 50, most preferably from 4 to 25, centipoises at temperature of from room temperature to 50°C, most particularly at temperatures of from 15° to 35°C.

The extremely low viscosity of the particularly preferred ε-caprolactam adducts with methanol, ethanol, propanol, chloroethanol or trichloroethanol, and also the demonstrable reduction in the carbonyl group frequency of the ε-caprolactam in the infra-red spectrum of these adducts towards shorter wavelengths, which is particularly noticeable in the addition products with more acidic alcohol components such as trichloroethanol, chloroethanol and, more particularly, with phenol and substituted phenols, is indicative of the fact that addition compounds with hydrogen bonds, for example of the type:

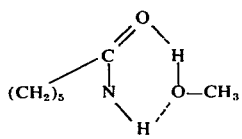

are formed in large measure in the adducts obtained in accordance with the invention.

The novel adducts obtainable by the process according to the invention, or their solutions in the excess of alcohol or thioalcohol which is optionally used, are excellent solvents for a wide variety of substances which are substantially or completely insoluble in water or organic solvents, and show surprising properties. For example, the addition compounds of 1 mol of ε-caprolactam (m.p. 70°C) with a variety of different monohydric alcohols, diols or triols, such as trimethylol propane, are liquids which are thinly viscous and crystal-clear at room temperature, have a surprisingly low viscosity and can be stored for indefinite periods. Apart from their miscibility with water, another particularly noticeable feature of these addition compound of, for exmple, 1 mol of ε-caprolactam and 1 to 2 mols of methanol, ethanol, chloroethanol, etylene glycol, glycerin and trimethylol propane, is their outstanding miscibility with a variety of different liquid hydrophobic solvents, and their remarkable dissolving powder for compounds containing urea groups, urethane groups or triazine groups, and for a number of salts of organic bases, and also for salts of carbamic acid and betaine-like salts of carbonic acid with polyamines.

The reactivity of the alcohol component, for example in adducts of any monofunctional alcohols, with respect to monoisocyanates and polyisocyanates is considerably increased, as can be demonstrated particularly clearly in the case of substantially non-reactive aliphatic, cycloaliphatic and araliphatic diisocyanates (see Examples 6, 7 and 9). According to these Examples, hydroxyl components such as methanol, ethanol, ethylene glycol and 1,4-butylene glycol in these addition compounds are generally highly activated for NCO reactions and show an increase in their reactivity of from 150 to 250 times, based on the uncatalysed OH/NCO reaction.

To prepare the new addition compounds, the cyclic amides or azalactams, preferably ε-caprolactam or 1-N-hexahydro-1,4-diazepin-3-one, are simply mixed, rubbed or stirred with a monohydroxyl, polyhydroxyl or mercapto compound, optionally under a little heat, the liquid addition compound being formed in a matter of minutes. As can be seen from the Examples, they are crystal-clear liquids with surprisingly low viscosities at room temperature or at slightly elevated temperature and, accordingly, can be used as highly effective solvents and reagents for a variety of different substances.

These new solvents can also be prepared, however, by concentrating dilute, alcoholic solutions of cyclic lactams by distillation, and stopping distillation when, for example, 1 to 4 mols of monohydric alcohols or at least 0.3 hydroxyl group equivalent of a polyhydroxy or SH compound are present in the thinly viscous liquids per mol of ε-caprolactam.

Volatile alcohols or thioalcohols in vapour form can, of course, also be introduced into the molten or liquid lactams and/or azalactams, until the required ratio of lactam or azalactam to the hydroxyl or SH compound is reached. It is also possible for addition products of monohydric alcohols (at least 1:1) of low boiling point to be mixed with monohydric alcohols or polyhydric alcohols of high boiling point and for the more volatile alcohol to be removed from the mixture.

In a modified embodiment, the addition compounds can also be produced, for example, by hydrogenating readily reducible carbonyl compounds, such as acetaldehyde, acetone or methyl ethyl ketone, dissolved in lactams that are hardly affected by conventional hydrogenation catalysts, or by splitting up compounds containing oxirane groups by hydrogenation, or by preparing the corresponding halogen-containing or amino-group-containing addition products from lactams and from halogen or aminoalcohols formed in situ simply by introducing hydrohalic acids or ammonia and amines into lactam/oxirane mixtures. The mixtures or addition compounds can, of course, also be prepared from lactams prepared in situ in suitable, for example high-boiling, alcohols by ring closure of corresponding aminocarboxylic acids, and distilling to remove the water that is formed. It is also possible to prepare mercaptans and polymercaptans in situ from suitable reactive halogen compounds and sodium hydrogen sulphide, in lactams as solvents.

The lactam preferably used for the production of the addition compounds is ε-caprolactam, which is produced commercially on a large scale. Any cyclic amides such as propiolactam, butyrolactam, valerolactam, dodecalactam and mixtures thereof are, however, also suitable.

Preferred lactams from the group of azalactams whose production and purification include 1-N-alkyl- and cyclohexyl- or aralkyl-hexahydro-1,4-diazepin-3-ones, especially 1-N-methyl-hexahydro-1,4-diazepin-3-one whose production is described in Example 15.

As can be seen from the following Examples, the adducts obtainable by the process according to the invention, for example from crystallised ε-caprolactam and 1 mol of ethanol or chloroethanol, are thinly viscous liquids which have a viscosity of only 3 to 5 centipoises at 28°C and which are able to dissolve a variety of different, substantially insoluble, substituted ureas, substantially insoluble urethanes, plant protection agents or substantially insoluble dyes under the influence of heat in high concentration. High molecular weight polyvinyl chloride can also be dissolved, over remarkably short periods, to give stable solutions that are unaffected by storage. The same applies as regards the ε-caprolactam adducts with methanol and numerous other alcohols, which are all potential solvents for polyvinyl chloride, acrylates, vinyl acetate and their copolymers, although it is generally known that methanol itself is a popular precipitant, for example for polyvinyl chloride.

By virtue of the process according to the invention, it is possible, either through variation of the lactams or, more particularly, through variation of the components containing hydroxyl groups and mercapto groups, which can be either hydrophilic or hydrophobic, to prepare solvents whose consitution is adapted to the substance to be dissolved, whether in the form of a plant protection agent, a substantially insoluble optical brightener, or a high molecular weight diisocyanate polyaddition product, so that maximum solubilities of these otherwise substantially insoluble substances can be obtained in this way.

The adducts of lactams with secondary alcohols whose molecule contains cyclic acetal groups of formaldehyde, acetaldehyde or acrolein, and alcohols whose molecule contains carbonyl or oxirane groups (see Table 1) also show remarkably low viscosity and a high dissolving power for high molecular weight polyurethanes, ureas, disubstituted ureas, urethanes, isocyanurates, derivatives of cyanuric acid chloride, a variety of different dyes and numerous metal salts such as nickel, manganese, copper or magnesium halides, lithium chloride, lithium iodide, calcium chloride, and betaine-like salts of carbon dioxide and carbon disulphide with primary amines and polyamines, optionally in admixture with dimethyl formamide.

The novel compounds are also eminently suitable for dissolving in high concentrations the following substances which are also substantially insoluble in water and organic solvents:

Urea derivatives, amides, semicarbazides, urethanes, polyurethanes, isocyanates, cyanuric acid esters, reaction products of cyanuric acid chloride with a variety of different substituted aliphatic, cycloaliphatic and aromatic amino derivatives, purine derivatives, carbodiimides and polycarbodiimides. They also dissolve plant protection agents which are difficult to dissolve in water such as O,O-diethyl-O-(2-quinoxalyl)-thiophosphate, a variety of different quinoxaline and quinazoline derivatives and 1-(3,4-dichloroanilino)-1-formylamino-2,2,2-trichloroethane, which is effective against mildew. Also to be recommended is the dissolution and recrystallisation of, for example, cereal herbicides such as 1,3-dimethyl-3-(2-benzthiazolyl)-urea and its purification with the addition product of 1 mol of methanol or 1 mol of ethanol with 1 mol of caprolactam, in which case the herbicide is obtained in a highly crystalline form. The mixtures or addition compounds are also useful solvents and formulating agents for diethyl-O-nitrophenyl esters of thiophosphoric acid; the addition product of chloral with dimethyl phosphate; imidazolines substituted in the 2-position, for example 2-heptadecyl imidazoline; imidazole; 2-methylimidazole; benzimidazole, mercaptobenzimidazole; 2,4-dichlorophenoxy acetic acid and derivatives thereof, such as its amides, for example the N-methylamide, N-ethylamide and N-butylamide; 2-methyl-4-chlorophenoxy acetic acid and its amide and N-substituted amides; 4-(2,4-dichlorophenoxy)-butyric acid; trichloroacetamide; 2,2-dichloropropionic acid; 2,2-dichloropropionamide; the N-methylol compounds of 2,2-dichloropropionic acid amide; 2,2-dichloropropionic acid amide-N-methylol methyl ether; chloroacetic acid diallyl amide; urethanes such as N-(3-chlorophenyl)-carbamic acid isopropyl ester; N-(4-chlorophenyl)-N,N'-dimethyl urea; urethanes of aromatic isocyanates optionally containing several chlorine atoms with isopropanol, or methyl isocyanate and isopropanol. They can also be used for halogen-containing triazines such as 2-chloro-4,6-bis-ethylamino-s-triazine; formyl compounds of amino guanidine; 3-aminotriazole; N-cyclohexyl-N-dimethyl urea; disodium ethylene bis-dithiocarbamate; 5-chloro-2-hydroxybenzene-1-carboxylic acid-n-amyl amide; and the methylol compound of 5-chloro-2-hydroxybenzene-1-carboxylic acid amide.

The mixtures or addition compounds according to the invention are also valuable solvents and formulating agents for a number of substantially insoluble dyes, azo- and anthraquinone-dyes, and also substantially non-flammable solvents for carrying out the recrystallisation and purification of commercial products.

The addition compounds according to the invention are also suitable for use as solvents for recrystallising and purifying many conventional optical brighteners from the class of 4,4'-diaminostilbene disulphonic acid derivatives, because they often do not dissolve relatively high molecular weight impurities, also because the substances suspended in and impurities present in the commercial products can readily be filtered off from the solutions and further because resin-like impurities in these solvents can only form colloidal solutions with difficulty. The new solvents are also suitable for purifying a variety of different coumarin derivatives and optical brighteners from the group of pyrazoline derivatives, for example:

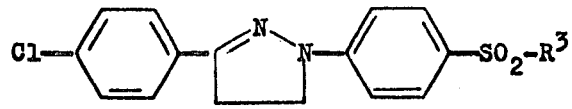

where
$R^3 = NH_2$, $-NH-CH_2CH_2OH$, or $-(CH_2)_2-OH$
which can be freed particularly effectively from impurities by recrystallisation, especially in the 1:1 addition products of caprolactam with 1 mol excess of alcohol such as methanol, ethanol or chloroethanol.

Another particular advantage of these new compounds is their miscibility with water, so that dissolved substances can readily be filtered from a variety of different classes of compounds by the addition of water and the solvent can be economically recovered, especially in the case of ε-caprolactam/diol (1:1) adducts, without giving off any toxic solvent vapours into the atmosphere, simply by removing water followed by concentration to a caprolactam: diol ratio of 1:1. Another factor of particular interest is the greater degree of safety attending recrystallisations carried out on an industrial scale, because in many instances these mixtures or addition compounds show reduced flammability or, in many instances, will only ignite at extremely high temperatures. Other decisive technical and practical advantages are the extremely low volatility, especially of the addition products of 1 mol of caprolactam with 1 to 2 mols of polyfunctional alcohols, such as ethylene glycol or diethylene glycol, but more particularly in the considerably lower toxicity of ε-caprolactam and suitable selected hydroxyl compounds, for example, than that of dimethyl formamide, dimethyl acetamide or dimethyl sulphoxide.

The high dissolving power of the addition compounds also used as solvents in accordance with the invention for metal salts, nickel chloride, iron chlorides, manganese-II-chloride, lithium chloride, lithium bromide and lithium iodide, for hydrochlorides of a variety of different organic bases, and for betaine-like salts of carbonic acid with a variety of different organic amines and polyamines, makes it possible to use the addition products for special reactions, especially when the reaction conditions selected are such that ε-caprolactam, for example, or the alcohol used show little or no co-reaction. The high solubility and the possibility of producing liquid calcium chloride solutions in the mixtures of addition compounds according to the invention makes it possible to produce organic/inorganic liquids which have hardly any corrosive effect, are extremely active against ice and slippery surfaces, which have a quick thawing effect, and which are, in particular, easy to dispense in measured quantities and to spray because they are liquids.

Moreover, the new solutions of the adducts, especially 1:1 addition products of ε-caprolactam with an excess of 1 mol of alcohol such as methanol, ethanol, isopropanol, t-butanol, chloroethanol and benzyl alcohol, afford many other advantages in the polymerisation, copolymerisation and graft polymerisation of vinyl and vinylidene monomers. They are particularly suitable for dissolving surprisingly high quanties of non-hydrophilic vinyl and vinylidene monomers, for example vinyl chloride, vinylidene chloride, vinyl acetate, acrylic esters, styrene, β-methyl styrene and chlorobutadienr, so that polymerisation reactions can be carried out in them to give concentrated solutions or suspensions of the polymers, copolymers or graft polymers in these solvents. The addition compounds can also be used as effective solvents for already prepared polymers, copolymers and graft polymers. The polymers can readily be precipitated from the resulting solutions by the addition of water and subsequently purified just as easily.

In addition, the addition compounds according to the invention, when used as reactive liquid solvents, afford possibilities in the control of diisocyanate polyaddition reactions, for example, because the alcohol components are highly activated, as shown by Examples 6, 7 and 9. Accordingly, the liquid trimethylol propane can readily be converted by adduct formation into crosslinked hard foams. In addition, the addition compounds are particularly suitable for carrying out fast polyaddition reactions of the kind encountered in epoxide chemistry, especially with a variety of different highly reactive polyamines containing primary and secondary amino groups, and also fast polycondensation reactions where the reactivity of the reagent is so high that substantially non-reactive caprolactam and the alcohol used for adduct formation do not take part to any appreciable extent in the polyaddition or polycondensation reaction. Examples of extremely fast reactions include polycondensations of N,N'-carbamic acid chlorides with polyamines; phosgene with polyamines, polycarboxylic acid chlorides with polyamines; benzoquinone with polyamines; cyanuric acid chlorides with polyamines; and pyrimidine halides with polyamines. Once again, working up of the polymers formed is very much easier, especially in the addition products of 1 mol of ε-caprolactam with 1 mol of methanol, ethanol or t-butanol, compared with other conventional solvents and, in addition, in the formation of extremely high molecular weight of even pigment-like powdered solids, the end products can readily be filtered or precipitated by the addition of water.

The addition compounds according to the invention are also interesting solvents for carrying out fast reactions of the kind encountered in aminoplast and phenoplast chemistry, especially when these reactions take place at high velocity and N-methylol lactams are preferentially formed, for example in the formation of powdered crosslinked hexahydrotriazines from hexamethyl diamine and formaldehyde, or pentamethylene diamine and formaldehyde; condensation of benzoquinone and naphthoquinone with aliphatic, cycloaliphatic, araliphatic and aromatic diamines; and in all alkaline catalysed phenol-formaldehyde condensation reactions; because N-methylol caprolactam formed in this case and N-hemiacetals of the monoalcohol or polyalcohol used react quantitatively, accompanied by the elimination of formaldehyde, to form the thermostable o- and p-methylolated phenol and resol types so that, ultimately, the addition compounds according to the invention are continuously regenerated.

The liquid addition compounds according to the invention are also eminently suitable for use as reaction media for carrying out condensation reactions of polycarboxylic acid esters or cyclic dicarboxylic acid anhydrides with polyamines, and for polycondensation of amino acid esters and/or free amino acids amongst themselves, optionally in the presence of cyclohexyl carbodiimide.

The addition compounds according to the invention have a wide variety of practical uses and their versatility is enhanced by virtue of the fact that, in general, it is possible to dissolve and, if desired, recrystallise compounds capable of forming hydrogen bonds and which contain, in the molecule or as a ring segment of a heterocyclic grouping, at least one of the following groups:

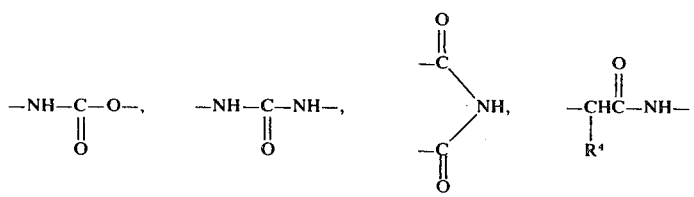

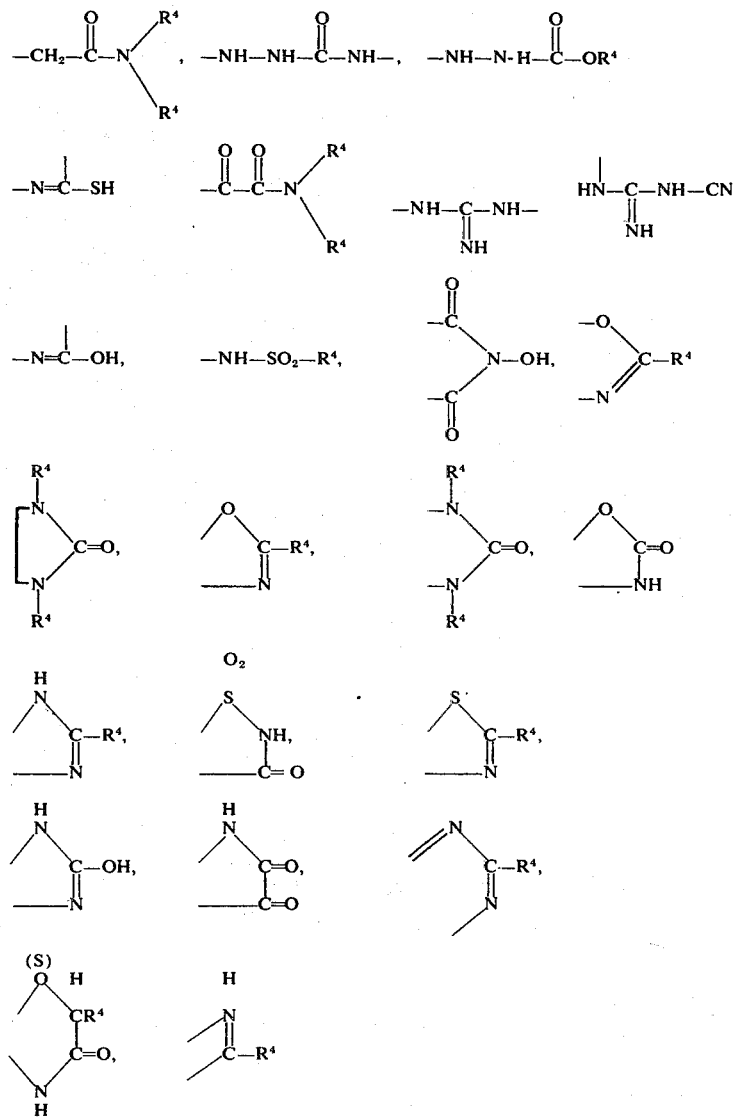

wherein

R[4] represents hydrogen or an optionally substituted aliphatic, cycloaliphatic, araliphatic, aromatic or heterocyclic radical, a halogen atom, an aminoalkylamino, dialkylamino, hydroxy or mercapto group.

The parts quoted in the following Examples are parts by weight unless otherwise stated.

EXAMPLE 1

Batches of 10 mols of liquid, crystalline or molten lactams are reacted at 50°C with 10 mols of organic monohydroxyl compounds with the constitutions and in the quantities by weight indicated in Table 2. Even when crystalline ε-caprolactam of m.p. 70°C is used, liquid mixtures or addition products which are crystal-clear and thinly viscous at 29°C and which have a high dissolving power for a variety of different substances that are substantially insoluble or completely insoluble in water or organic solvents, are obtained in every instance. The 1:1 addition compounds obtained show the following conspicuously low viscosities.

Table 2

| No. | Lactam | Parts by weight | Alcohol | Parts by weight | Molar ratio | η in centipoises |
|---|---|---|---|---|---|---|
| 1 | $(CH_2)_5$\<C=O / NH | 1131 | $CH_3OH$ | 321 | 1:1 | 5.9 (28°C) |
| 2 | " | 1131 | $C_2H_5OH$ | 461 | 1:1 | 7.3 (28°C) |
| 3 | " | 1131 | $ClCH_2.CH_2OH$ | 805 | 1:1 | 17.5 (21°C) |
| 4 | " | 1131 | $CCl_3—CH_2—OH$ | 1495 | 1:1 | 12.4 (21°C) |
| 5 | " | 1131 | $C_2H_3—C(CH_2—O)(HO—CH_2)(CH_2—O)CH_2$ | 1461 | 1:1 | 18.5 (21°C) |

Table 2-continued

| No. | Lactam | Parts by weight | Alcohol | Parts by weight | Molar ratio | η in centipoises |
|---|---|---|---|---|---|---|
| 6 | " | 1131 | HO—CH(CH₂—O)(CH₂—O)CH₂ | 1040 | 1:1 | 24.6 (21°C) |
| 7 | (CH₂)₅—NH with C=O | 1131 | HO—CH₂—CH(O)—CH₂ | 740 | 1:1 | 19.7 (21°C) |
| 8 | " | 1131 | C₂H₅—C(CH₂—O)(HOCH₂)(CH₂—O)C=O | 1600 | 1:1 | 26.7 (21°C) |
| 9 | " | 1131 | C₂H₅—C(CH₂—O)(HOCH₂)(CH₂—O)CH—CH₃ | 1480 | 1:1 | 28.9 (21°C) |
| 10 | (CH₂)₄—NH with C=O | 991 | CH₃OH | 321 | 1:1 | 5.2 (21°C) |
| 11 | (CH₂)₃—NH with C=O | 751 | CH₃OH | 321 | 1:1 | 4.5 (21°C) |
| 12 | (CH₂)₅—NH with C=O | 1131 | C₆H₅CH₂OH | 1080 | 1:1 | 10.5 (21°C) |
| 13 | " | 1131 | CH₂=CH—CH₂OH | 580 | 1:1 | 6.4 (21°C) |

EXAMPLE 2

The procedure is exactly the same as in Example 1, batches of 1 mol of 1-N-methyl-hexahydro-diazepin-3-one, a 7-membered crystallised lactam derivative of m.p. 91°C (see Example 15 for production) each being reacted with 1 mol of organic monohydroxyl compound in the quantities by weight specified in Table 3. Mixtures or addition products which are crystal-clear and thinly liquid at a temperature of 55°C and which have the remarkably low viscosities specified in Table 3 are obtained.

Table 3

| No. | Lactam | Parts by weight | Alcohol | Parts by weight | Molar ratio | Viscosity in centipoises |
|---|---|---|---|---|---|---|
| 1 | CH₃—N(CH₂)(CH₂)₃ ring with C=O, NH | 128.1 | CH₃OH | 32 | 1:1 | 2.5 (45°C) |
| 2 | " | 128.1 | C₂H₅OH | 46 | 1:1 | 3.8 (45°C) |
| 3 | " | 128.1 | CCl₃—CH₂OH | 149.5 | 1:1 | 7.4 (45°C) |
| 4 | " | 128.1 | Cl—CH₂—CH₂—OH | 80.5 | 1:1 | 11.5 (45°C) |

If the alcohols used in Tables 2 and 3 are replaced by 1 mol each of isopropanol, n-butanol, t-butanol, aminoethanol, dimethylaminoethanol and oleyl alcohol, readily filterable thinly viscous addition products with the following viscosities are obtained at 28° to 45°C with 1 mol of ε-caprolactam.

1 mol of ε-caprolactam . 1 mol of t-butanol: 12.5 cP at 28°C 1 mol of ε-caprolactam . 1 mol isopropanol: 7.6 cP at 28°C 1 mol of ε-caprolactam . 1 mol aminoethanol: 32.5 cP at 39°C 1 mol of ε-caprolactam . 1 mol dimethylaminoethanol: 28.5 cP at 28°C 1 mol of ε-caprolactam . 1 mol oleyl alcohol: 34.9 cP at 28°C

EXAMPLE 3

The procedure is as in Example 1, except that 64 parts by weight of methanol (2mols) are used to 113 parts by weight of ε-caprolactam (1 mol). Crystal-clear thinly viscous solutions are obtained in which the readily crystallised ε-caprolactam cannot be crystallised even at temperatures around −25°C.

| Viscosity: | 1 mol of ε-caprolactam + 2 mols of methanol: | 3.8 cP at 21°C |
|---|---|---|
| Viscosity: | 1 mol of ε-caprolactam + 2 mols of ethanol: | 4.3 cP at 21°C |

EXAMPLE 4

The procedure is as described in Example 3 except that 38.4 parts by weight of methanol (1.2 mols) are used to 113 parts by weight of ε-caprolactam (1 mol). A thinly viscous liquid with a viscosity of 4.2 centipoises at 21°C is obtained. It does not show any tendency towards crystallisation at +9°C, can be stored for an indefinite period and only small fractions of crystallised ε-caprolactam separate at temperatures around −10°C.

EXAMPLE 5

The procedure is as in Example 4 except that 55.2 parts by weight of absolute ethanol (1.2 mols) are used to 113 parts by weight of ε-caprolactam (1 mol). A low viscosity liquid is obtained, which has a viscosity of 4.8 centipoises at 21°C and which does not show any tendency for ε-caprolactam to separate at temperatures of up to about 7°C.

EXAMPLE 6

This Example demonstrates the surprisingly high activation of the alcohol component, probably attached through hydrogen bonds, in the ε-caprolactam:-methanol (1:1) adduct assumed to correspond to the formula:

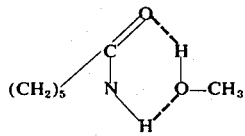

for carrying out isocyanate reactions.

Comparison Test (a)

This comparison test shows that ε-caprolactam reacts very slowly with hexamethylene diisocyanate at 30° to 40°C. Measurements are taken on the time required to obtain a 50% isocyanate or caprolactam conversion in accordance with the idealised reaction equation:

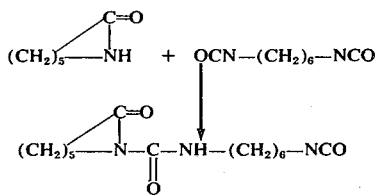

In order to obtain exact comparison figures, ε-caprolactam is dissolved in benzene to give a 78% by weight solution in this test. Accordingly, the concentration in this solution corresponds to the concentration of ε-caprolactam in the ε-caprolactam:methanol (1:1) addition compound (78% by weight of caprolactam).

33.9 Parts by weight of ε-caprolactam (0.3 mol) are dissolved together with 9.6 parts by weight of benzene at 60°C to form a 78% by weight solution. The resulting solution is cooled and 50.4 parts by weight (0.3 mol) of hexamethylene diisocyanate is added to it in one portion at approximately 40°C. Despite spontaneous admixture, there are no signs of an increase in temperature, nor is there any evidence of an increase in temperature after gentle heating to 40°C. The NCO value of the reaction mixture decreases very slowly, and falls over a period of 18 hours at 30°C from 26.8% NCO to 24% NCO and, after another 24 hours, to 21.2% NCO. It is only after a total of 80 hours that the theoretical NCO value of approximately 20.2% NCO for half the ε-caprolactam conversion is obtained. This test demonstrates that ε-caprolactam is substantially nonreactive in the uncatalysed reaction with hexamethylene diisocyanate. Half-life: 80 hours.

Comparison Test (b)

In order to obtain exact comparison figures for the non-catalysed methanol/hexamethylene diisocyanate reaction in accordance with the idealised equation:

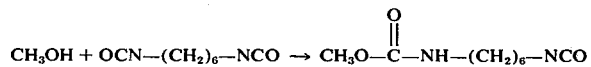

methanol is dissolved in benzene to give a solution whose concentration corresponds to the concentration of methanol in the caprolactam:methanol (1:1) adduct, i.e. a concentration of 22% by weight. The time required to obtain a 50% methanol conversion (half-life) is measured.

9.6 Parts by weight of methanol (0.3 mol) are dissolved with 33.9 parts by weight of anhydrous benzene to form a solution containing 22% by weight of methanol, followed by the addition in one portion at 22°C of 50.4 parts by weight of hexamethylene diisocyanate (0.3 mol). A very slow reaction with hardly any increase in temperature begins. According to continuous NCO titration, half the methanol conversion is only obtained after 8 hours, and the reaction mixture shows an NCO value of 20.2% for half the methanol conversion. Half-life: 8 hours.

Comparison Test (c)

If in Comparison Test (b) the solvent benzene is replaced by N-methyl caprolactam:

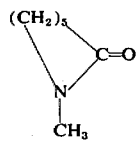

the addition compounds according to the invention cannot be formed. The half-life for half the methanol conversion is 8.2 hours. NCO value: 20.2%.

Comparison Test (d)

50.4 Parts by weight (0.3 mol) of hexamethylene diisocyanate are added in one portion at 26°C to 43.5 parts by weight (0.3 mol) of the ε-caprolactam:methanol (1:1) addition compound. The high activation of the methanol is reflected in an increase in temperature, which begins after only 30 seconds mixing so that, in comparison with Comparison Tests (b) and (c), a temperature of 71°C is measured after only 2 minutes and a temperature of 120°C after only 4 minutes and the conversion is already quantitative. If the same reaction is carried out with cooling at 25°C in order to determine the half-life time, a 50% methanol conversion is obtained after only aout 2 minutes in comparison with Comparison Tests (b) and (c). This test shos that the methanol in the ε-caprolactam:methanol (1:1) addition compound is very highly activated and that, on the basis of the half-lives, the reactivity is some 246 times (!) higher than it is in the benzene:methanol system or in the N-methyl caprolactam:methanol system. If the aforementioned ε-caprolactam addition compound is replaced by 1:1 adducts of ε-caprolactam with ethanol, ethylene glycol or 1,4-butane diol, the hydroxyl compounds are once again highly activated for NCO reactions and show an increase in their reactivity of from 150 to 250 times (!) compared with the uncatalysed OH/NCO reaction.

EXAMPLE 7

By way of amplification of Example 6, Comparison Test (d), this Example shows that only the alcohol component in the ε-caprolactam:methanol addition compounds is activated and that the reaction of hexamethylene diisocyanate in accordance with the equation:

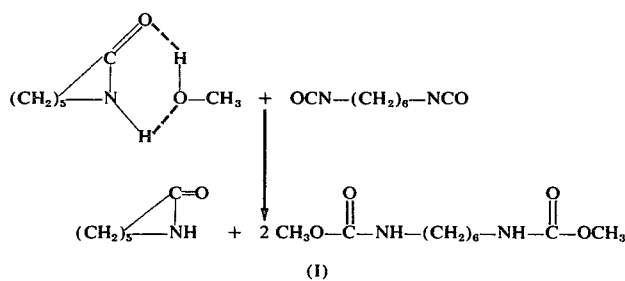

takes place selectively to an extent of greater than 98% by weight to form the diurethane (I), whilst, in consistency with Comparison Tests (a) and (c), ε-caprolactam reacts chemically with the diisocyanate at a very much lower rate.

43.5 Parts by weight (0.3 mol) of the ε-caprolactam:methanol (1:1) adduct are reacted with gently cooling at 26°C with 25.2 parts by weight (0.15 mol) of hexamethylene diisocyanate. The resulting diurethane crystallises out after only 30 minutes. The product is kept at room temperature for 20 hours. It is then diluted with 300 parts by weight of water and filtered off from the crystalline deposit. 32.5 g of a crystalline compound are obtained whose melting point, mixed melting point and elemental analysis are identical with those of the dimethyl urethane of hexamethylene diisocyanate. Yield: approximately 98% of the theoretical.

EXAMPLE 8

113 Parts by weight (1 mol) of ε-caprolactam are reacted respectively with:
   a. 64 parts by weight (2 mols) of methanol,
   b. 96 parts by weight (3 mols) of methanol,
   c. 128 parts by weight (4 mols) of methanol,
   d. 92 parts by weight (2 mols) of ethanol, and
   e. 138 parts by weight (3mols) of ethanol,
resulting in the formation of low viscosity liquids which do not show any tendency towards crystallisation at 0°C, are miscible with one another in any ratios and, either as such or in admixture, constitute excellent solvents for compounds that are insoluble in water, for example N-phenyl urea, N,N'-diphenyl urea and benzthiazolyl ureas. To this end, 15 to 20% by weight of the substantially insoluble substances are dissolved, being obtained in crystalline form on cooling.

If 25 parts by weight of a substantially analytically pure optical brightener with the constitution:

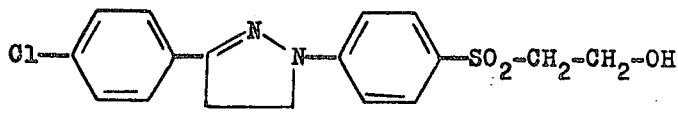

are dissolved in 100 parts by weight of the liquid mixtures or addition compound of 1 mol of ε-caprolactam and 1.2 mols of methanol, 0.5% by weight of resin-like brown coloured fractions can readily be separated by filtration, and the pyrazoline brightener is precipitated on cooling in the form of gold-yellow crystalites of high purity.

EXAMPLE 9

This Example is clear proof of the considerable extent to which the viscosity of polyols, such as glycerine or trimethylol propane for example, is reduced by adduct formation with even relatively high-melting lactams such as ε-caprolactam (m.p. 70°C).

Pure glycerine has a viscosity of 190 cP at 21°C. Pure trimethylol propane crystallises at room temperature, whilst impure supercooled melts have a viscosity at 21°C of 3850 cP.

Batches of 113 parts by weight of crystalline ε-caprolactam of m.p. 70°C (1 mol) are fused at 70°C with 92 parts by weight (1 mol) of pure glycerine with the above viscosity or with 134 parts by weight (1 mol) of trimethylol propane. After cooling to room temperature, low viscosity addition compounds, in the form of clear liquids which do not shown any tendency towards crystallisation even at 0°C, are obtained.

These two addition compounds are outstanding antifreeze agents, either as such or in admixture with 1 to 3 mols of water, or even in the form of 1:1 mixtures. The addition product of 1 mol of ε-caprolactam and 1 mol of trimethylol propane, which is liquid at room temperature, can be used for the production of foams by reacting it with up to 3 mols of tolylene diisocyanate to produce the 1:1 addition compounds. Liquids of surprisingly low viscosity are obtained:

Table 4

| No. | Lactam | Polyol | Molar ratio | $\eta$ in centipoises |
|---|---|---|---|---|
| 1 | (CH$_2$)$_5$—NH, C=O | HO—CH$_2$—CH$_2$OH | 1:1 | 8.3 (21°C) |
| 2 | (CH$_2$)$_5$—NH, C=O | HO—CH$_2$—CH$_2$—CH$_2$OH | 1:1 | 10.5 (21°C) |
| 3 | (CH$_2$)$_5$—NH, C=O | HO—(CH$_2$)$_4$—OH | 1:1 | 11.2 (21°C) |
| 4 | (CH$_2$)$_5$—NH, C=O | HO—CH$_2$—C(CH$_3$)$_2$—CH$_2$OH | 1:1 | 60.4 (21°C) |
| 5 | (CH$_2$)$_5$—NH, C=O | HO—CH$_2$—CH$_2$—O—CH$_2$—CH$_2$OH | 1:1 | 9.8 (21°C) |
| 6 | (CH$_2$)$_5$—NH, C=O | HO—(CH$_2$—CH$_2$—O)$_3$—OH | 1:1 | 10.5 (21°C) |
| 7 | (CH$_2$)$_5$—NH, C=O | HO—CH$_2$—CH$_2$—N(CH$_3$)—CH$_2$—CH$_2$OH | 1:1 | 11.8 (21°C) |
| 8 | (CH$_2$)$_5$—NH, C=O | HO—CH$_2$—CH$_2$—N(C$_6$H$_{11}$)—CH$_2$—CH$_2$OH | 1:1 | 18.5 (21°C) |
| 9 | (CH$_2$)$_5$—NH, C=O (113 parts by weight) | HO—CH$_2$—C$_6$H$_4$—CH$_2$OH | 1:1 | 56 (29°C) |
| 10 | (CH$_2$)$_4$—NH, C=O (129 parts by weight) | HO—CH$_2$—CH$_2$—O, HO—CH$_2$—CH$_2$ | 1:1 | 7.8 (21°C) |
| 11 | (CH$_2$)$_3$—NH, C=O | HO—CH$_2$—CH(OH)—CH$_2$OH | 1:1 | 98.5 (23°C) |
| 12 | CH$_3$,CH$_2$ N C=O (CH$_2$)$_3$—NH | HO—CH$_2$—CH(OH)—CH$_2$OH | 1:1 | 105 (21°C) |
| 13 | (CH$_2$)$_3$—NH, C=O | HO—CH$_2$—CH$_2$—OH | 1:1 | 5.1 (21°C) |
| 14 | (CH$_2$)$_5$—NH, C=O | C(CH$_2$OH)$_4$ | 1:1 | 150 (29°C) | and water as expanding agents, resulting in the formation of hard foams with most of the caprolactam incorporated therein.

EXAMPLE 10

The procedure is as in Example 1, except that the polyhydroxyl compounds specified in Table 4 are used

EXAMPLE 11

The procedure is as in Example 10, except that the saturated alcohols, unsaturated alcohols, alcohols containing ester groups, mercaptans and semi-acetals of mono- and poly-hydroxy compounds specified in Table 5 are used to produce the 1:; addition compounds. Low viscosity mixtures or addition compounds with the viscosities specified in Table 5 are obtained.

Table 5

| No. | Lactam | Alcohol | Molar ratio | η in centipoises (21°C) |
|---|---|---|---|---|
| 1 | (CH₂)₅⟨C=O/NH⟩ | CH₂=CH—CH₂OH | 1:1 | 6.4 |
| 2 | (CH₂)₅⟨C=O/NH⟩ | CH₂=C(CH₃)—O—CH₂—C(CH₃)(H)—OH | 1:1 | 14.8 |
| 3 | (CH₂)₅⟨C=O/NH⟩ | C₄H₉SH | 1:1 | 35.6 |
| 4 | (CH₂)₅⟨C=O/NH⟩ | CH₃—(CH₂)₁₁SH | 1:1 | 42 |
| 5 | (CH₂)₅⟨C=O/NH⟩ | HO—CH₂—CH₂\\S/CH₂—CH₂—OH | 1:1 | 11.5 |
| 6 | (CH₂)₅⟨C=O/NH⟩ | HS—CH₂—CH₂—OH | 1:1 | 10.4 |
| 7 | (CH₂)₅⟨C=O/NH⟩ | Cl—CH₂—CH(OH)—CH₂Cl | 1:1 | 11 (32°C) |
| 8 | (CH₂)₅⟨C=O/NH⟩ | oleyl alcohol | 1:1 | 38.5 (25°C) |
| 9 | (CH₂)₅⟨C=O/NH⟩ | C₆H₅—CH₂OH | 1:1 | 10.8 (25°C) |
| 10 | (CH₂)₅⟨C=O/NH⟩ | C₆H₅—CH₂—CH₂OH | 1:1 | 8.3 (25°C) |
| 11 | (CH₂)₅⟨C=O/NH⟩ | furfuryl alcohol (CH=CH—O—C(CH₂OH)=CH) | 1:1 | 7.9 (25°C) |
| 12 | (CH₂)₅⟨C=O/NH⟩ | (CH₂)₅⟨C=O/N—CH₂OH⟩ | 1:1 | 25.6 (25°C) |
| 13 | (CH₂)₅⟨C=O/NH⟩ | CH₃—O—CH₂OH | 1:1 | 12.8 |
| 14 | (CH₂)₅⟨C=O/NH⟩ | C₂H₅—O—CH₂OH | 1:1 | 13.5 |
| 15 | (CH₂)₅⟨C=O/NH⟩ | HO—CH₂—O—CH₂—CH₂—OH | 1:1 | 10.2 |
| 16 | (CH₂)₅⟨C=O/NH⟩ | HO—CH₂—O—CH₂—CH(OH)—CH₂OH | 1:1 | 105 |
| 17 | (CH₂)₅⟨C=O/NH⟩ | p-C₆H₄[C(=O)—O—CH₂—CH₂—OH]₂ | 1:1 | 95 (35°C) |

Table 5-continued

| No. | Lactam | Alcohol | Molar ratio | η in centipoises (21°C) |
|---|---|---|---|---|
| 18 | (CH$_2$)$_5$ C=O / NH | CH$_3$—O—CH$_2$—CH$_2$OH | 1:1 | 8.5 (25°C) |
| 19 | (CH$_2$)$_5$ C=O / NH | CH(—O—CH$_2$OH)(CH$_2$CH$_2$—O—CH$_2$OH) | 1:1 | 10.5 (21°C) |
| 20 | (CH$_2$)$_5$ C=O / NH | HO—CH$_2$—OH | 1:1 | 8.7 (29°C) |
| 21 | (CH$_2$)$_5$ C=O / NH | HOCH$_2$CH$_2$—C(=O)—CH$_2$—CH$_2$OH | 1:1 | 14.5 (29°C) |
| 22 | (CH$_2$)$_5$ C=O / NH | HOCH$_2$—(cyclohexane with C=O)—CH$_2$OH | 1:1 | 58 (29°C) |

The 1:1 addition compounds prepared from hemiacetals or formaldehyde hydrate, numbered 13, 14, 15, 16, 19 and 20 in Table 5 are prepared by mixing crystalline or liquid lactams with liquid hemiacetals or formaldehyde hydrate at 25° to 75°C with thorough stirring. The low viscosity solutions obtained remain stable for several hours without any appreciable methylolation of the lactam.

EXAMPLE 12

The following Examples demonstrate the use of the addition compounds according to the invention as solvents for high molecular weight polyvinyl chloride, polyvinyl acetate and polymethyl acrylate, and the advantageous purification or the dissolved polymers by precipitation with water.

At a temperature of 70°C
a. 60 parts by weight of high molecular weight polyvinyl chloride (molecular weight 25,000) are dissolved in 303 parts by weight of a solution of the adduct prepared from 226 parts by weight of caprolactam (2 mols) and 76.8 parts by weight of methanol (2.4 mols),
b. 40 parts by weight of high molecular polyvinyl acetate (molecular weight 30,000) are dissolved in the solvent described above under a),
c. 60 parts by weight of a high molecular weight polymethyl acrylate (molecular weight 18,000) are dissolved in the solvent described above under a).

Satisfactorily pourable solutions are obtained in each instance (a) to (c). When added dropwise to water, the dissolved polymer is quantitatively precipitated in easily filterable form without any formation of hazy, substantially non-filterable mother liquors with colloidally dissolved polymer fractions. If the mother liquors (a) to (c) are freed from water in vacuo and the quantity of hydroxyl compound required for adduct formation is added to each, the solvents used in (a) to (c) are recovered in substantially quantitative yields.

EXAMPLE 13

This Example shows that vinyl monomers, for example, can readily be dissolved in the addition product of ε-caprolactam and methanol (1:1), or in a solution thereof in an excess of methanol. Batches of 100 parts by weight of the addition product of 1 mol of ε-caprolactam and 1.2 mols of methanol can be mixed with the following quantities of vinyl monomers without two liquid phases being formed:
a. 140 parts by weight vinyl acetate,
b. 125 parts by weight of methyl methacrylate,
c. 130 parts by weight of methyl acrylate,
d. 135 parts by weight of ethyl acrylate,
e. 118 parts by weight of styrene,
f. 140 parts by weight of acrylonitrile, and
g. 115 parts by weight of 3-chlorobutadiene.

Accordingly, the high solubility of the aforementioned vinyl monomers in the addition compounds according to the invention makes it possible to carry out simple polymerisation, copolymerisation and graft polymerisation reactions in these solvents with the advantage that the polymers obtained can readily be precipitated quantitatively by the addition of water, or can be purified by fractionation.

EXAMPLE 14

The 1-N-substituted hexahydro-1,4-diazepin-3-ones used in the preceding Examples are prepared in accordance with the following method of production for 1-N-methyl-hexahydro-1,4-diazepin-3-one, representing a generally applicable procedure for the synthesis of a variety of different 1-N-substituted azalactams.

A solution of 750 g of N-methyl-N-(2-cyanoethyl)glycine ethyl ester (prepared from methylaminopropionitrile and ethyl chloroacetate) in 1 liter of ethanol is hydrogenated in the presence of 60 g of Raney cobalt in an autoclave at a temperature of from 80° to 90°C and under a pressure of 100 to 120 atms. of hydrogen. The calculated quantity of hydrogen has been absorbed after about 1 hour. The hydrogenated solution is filtered off from the catalyst. The solid residue left after the ethanol has been evaporated is freed from any greases adhering to it by means of a little ethyl acetate, and the white product, which does not show any tendency towards discoloration in air, is fractionated in a high vacuum with 5 g of sodium methoxide. 424 g of 1-N-methyl-hexahydro-1,4-diazepin-3-one melting at 91°C are obtained.

EXAMPLE 15

This Example demonstrates the advantageous use of the compounds according to the invention or solutions thereof in excess alcohol or thioalcohol for carrying out fast condensation reactions.

The following diamines are dissolved in batches of 400 parts by weight of the solvent, thinly liquid at room temperature, derived from 1 mol of ε-caprolactam and 1.2 mols of methanol:

a. 92 parts by weight of hexamethylene diamine,
b. 92 parts by weight of hexamethylene diamine,
c. 134 parts by weight of isophorone diamine,
d. 100 parts by weight of ethylene diamine, and
e. 100 parts by weight of 1,3-diaminopropane.

The following are stirred into solutions (a) to (e) over periods of 10 minutes:

a'. 0.2 mol of bis-chlorocarbonic acid ester of 1,6-hexane diol,
b'. 0.2 mol of the bis-carbamic acid chloride of N,N'-diisopropyl hexamethylene diamine,
c'. 0.2 mol of a bis-chlorocarbonic acid ester of 1 mol of α,ω-dihydroxy polyethylene oxide (average molecular weight 2000) and 2 mols of phosgene,
d'. 0.2 mol of a bis-chlorocarbonic acid ester of 1 mol of α,ω-dihydroxy polybutylene oxide (average molecular weight 2000) and 2 mols of phosgene, and
e'. 0.2 mol of an α,ω-bis-carbamic acid chloride prepared from 1 mol of an α,ω-dihydroxy polyester of adipic acid/ethylene glycol (average molecular weight 2000) 2 mols of hexamethylene diisocyanate and 1 mol of anhydrous hydrochloric acid.

The following products corresponding to (a') to (e') are obtained in substantially quantitative yields without any appreciable reaction of the caprolactam or of the methanol present:

a''. α,ω-diaminourethanes: yield 73 parts by weight,
b''. α,ω-diaminodiureas: yield 59 parts by weight,
c''. α,ω-diaminodiurethanes: yield 218 parts by weight,
d''. α,ω-diaminodiurethanes: yield 205 parts by weight, and
e''. α,ω-diaminodiurethane diureas: yield 215 parts by weight, which are quantitatively precipitated from the ε-caprolactam:methanol adduct by the addition of 800 parts by weight of water.

EXAMPLE 16

This Example demonstrates the high dissolving power of the ε-caprolactam addition products for a variety of different hydrophobic α,ω-diurethanes with average molecular weights of from 2000 to 4000.

The following highly viscous α,ω-diurethanes, which can only be poured at 90°C, are dissolved at 90°C in batches of 250 parts by weight of the thinly liquid addition compound of 1 mol of ε-caprolactam and 1.2 mols of ethanol:

a. 250 parts by weight of an α,ω-diurethane prepared from 2 mols of phenol and 1 mol of an α,ω-diisocyanatodiurethane which was prepared from 1 mol of an α,ω-dihydroxy adipic acid/ethylene glycol polyester (average molecular weight 2000) and 2 mols of tolylene diisocyanate.
b. 250 parts by weight of an α,ω-diurethane prepared from 2 mols of phenol and 1 mol of an α,ω-diisocyanatodiurethane which was prepared from 1 mol of an α,ω-dihydroxy polypropylene glycol (average molecular weight 2000) and 2 mols of 4,4'-diisocyanato-diphenylmethane.
c. 250 parts by weight of an α,ω-diurethane prepared from 2 mols of methanol and 1 mol of an α,ω-diisocyanatodiurethane which was prepared from 1 mol of an α,ω-dihydroxy polythioether of thiodiglycol and hexane diol (70:30) (average molecular weight 4000) and 2 mols of tolylene diisocyanate.

Satisfactorily pourable 50% by weight solutions with the following viscosities at 35°C are obtained in each instance (a) to (c):

a. 390 cP at 35°C,
b. 280 cP at 35°C, and
c. 620 cP at 35°C.

EXAMPLE 17

This Example demonstrates the advantageous use of ε-caprolactam:methanol adducts as solvents for carrying out basically-catalysed condensation reactions of the kind encountered in phenoplast chemistry.

222 Parts by weight of 2,2'-bis-(4-hydroxyphenyl)-propane and 7 g of potassium carbonate are dissolved at 70°C in 700 parts by weight of a solvent derived from 1 mol of ε-caprolactam and 1.2 mols of methanol. 120 Parts by weight of paraformaldehyde are added, with thorough stirring, over a period of 2 hours. This is followed by stirring for 2 hours at 90°C, after which the clear solution is left to cool and the methylolated bisphenol is subsequently precipitated by the addition of 700 parts by weight of water. A readily soluble uncrosslinked addition product containing on average 3.4 methylol groups per mol of bisphenol is obtained in a yield of 320 parts by weight (98% of the theoretical). The thinly liquid slowly crystallising polymethylol phenol is freed from residues of caprolactam by shaking with water. Soften point: 58° to 63°C.

Although ε-caprolactam can be converted very easily with formaldehyde into N-methylol caprolactam in the presence of basic catalysts, the Example shows that it is continuously regenerated during condensation, because the methylolated 2,2-bis-(4-hydroxyphen 1)-propane is the thermally more stable compound. Despite its reactivity with respect to formaldehyde, therefore, the ε-caprolactam:methanol adduct is a genuine solvent which does not take any part in the reaction.

In an alternate embodiment, adducts of the invention can also be formed from alcohols of the formula G — (YH)$_n$ wherein G is an optionally substituted aromatic radical containing up to 24 carbon atoms, or an optionally substituted heterocyclic radical, Y represents oxygen or sulphur, n is an integer from 1 to 4, preferably from 1 to 3, most preferably 1 or 2, when Y represents oxygen, or n is an integer from 1 to 4, preferably 1 or 2, when Y represents sulphur.

The aromatic radicals contain up to 24 carbon atoms in the ring system, although aromatic hydrocarbons with up to 14, and more particularly with up to 10, carbon atoms are preferred, the benzene radical being particularly preferred. The following are examples of substituents of the aromatic radicals:

Halogens (preferably fluorine, chlorine or bromine), $NO_2$, lower alkyl, O-alkyl, S-alkyl, dialkylamino groups (each with preferably 1 to 4 carbon atoms per alkyl group), formyl or lower carboalkoxy groups (preferably 1 to 6 carbon atoms).

Optionally substituted heterocyclic radicals may be those having 3- to 7-membered hetero ring systems containing as hetero atoms oxygen, sulphur or nitrogen; the heterocyclic ring system can optionally also be anellated with benzene ring systems, while the OH group or the SH group can be attached to the hetero ring system, optionally through a methylene group. Those compounds in which an alcohol or SH group is attached to the heterocyclic ring system through a nitrogen atom, include in particular N-methylol caprolactam, N-methylol butyrolactam, N-methylol valerolactam and N-methylol propiolactam.

Substituents on the heterocyclic radical include:

$NO_2$, halogens (preferably fluorine, chlorine or bromine), lower alkyl, O-alkyl, S-alkyl or dialkylamino groups (each with 1 to 4 carbon atoms per alkyl group).

The following starting compounds containing phenolic hydroxyl groups and aromatic mercapto groups are suitable:

Phenol, all cresol isomers, mixtures thereof, chlorinated phenols and nitrophenols, methylolated phenols and methylolated cresols, 2-hydroxybenzamide, methyl and isobutyl salicylate, o- and p-salicylaldehyde, α- and β-naphthol, methylolated t-butyl phenols, aminophenols, β-hydroxy benzaldehyde, 2,3,-dihydroxyquinoxaline, 2-mercaptobenzimidazole and mercaptotriazole. All mono- or bis-hemiacetals of formaldehyde and chloral and the aforementioned polyphenols such as pyrocatechol, resorcinol 2,2-bis-(4'-hydroxyphenyl)-propane and tetrachloro compounds thereof, their oxethylation, propoxylation and their partially cyanoethylated derivatives and bis-hydroxybenzylamine.

Preferred mercaptans include thiophenol and substituted thiophenols. Preferred substituents on the phenyl radical of the thiophenol include halogens with the meanings already defined, alkyl radicals with 1 to 12, preferably with 1 to 4 carbon atoms and lower alkoxy groups, preferably with 1 to 4 carbon atoms and the nitro group.

EXAMPLE 18

The Examples summarised in Table 6 show that relatively acidic hydroxyl compounds, such as phenols, in conjunction with lactams, give addition compounds in the form of defined crystalline substances. Their infrared spectra show that the position of the carbonyl band of the ε-caprolactam is distinctly displaced towards lower wavelengths. For example, a solution of the ε-caprolactam: phenol (1:1) adduct mentioned in Table 6 in carbon tetrachloride shows a carbonyl band in the infra-red spectrum at 1659 cm$^{-1}$, whilst the carbonyl band of ε-caprolactam in carbon tetrachloride is situated at 1670 cm$^{-1}$.

Batches of 1 mol of the lactams specified in Table 4 are mixed with 1 mol of each of the aforementioned phenols at a temperature of 60°C. The addition compounds obtained are remarkably thinly liquid at 55°C and crystallise at room temperature into completely uniform, regularly developed crystal needles which, according to elemental analysis, also have the composition of 1:1 addition compounds.

Table 6

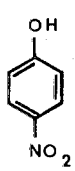

Table 6-continued

| No. | Lactam | Phenol Derivative | Molar ratio | $\eta$ in centipoises (30°C) |
|---|---|---|---|---|
| 5 | (CH₂)₅—C(=O)—NH | CH₃—C₆H₄—OH | 1:1 | 18 |
| 6 | (CH₂)₅—C(=O)—NH | CH₃O—C₆H₄—OH | 1:1 | 22 |
| 7 | (CH₂)₅—C(=O)—NH | 2-Cl-C₆H₄—OH | 1:1 | 15 |
| 8 | (CH₂)₅—C(=O)—NH | 3-Cl-C₆H₄—OH | 1:1 | 24 |

What is claimed is:

1. Adduct of a lactam selected from the group of epsilon-caprolactam, 1-N-methyl hexahydro-1,4-diazepin-3-one, propiolactam, butyrolactam, valerolactam and dodecalactam, with an alcohol selected from the group of methanol, ethanol, propanol, n-butanol, isopropanol, t-butanol, cyclohexanol, allyl alcohol, ethylene glycol monomethyl ether, benzyl alcohol, chloroethanol, fluoroethanol, trichloroethanol, trifluoroethanol, beta-hydroxypropylester of $C_{1-4}$ carboxylic acids, furfuryl alcohol, tetrahydrofurfuryl alcohol, n-butyl mercaptan, dodecyl mercaptan, mercaptoethanol, a hemiacetal of the foregoing alcohols with formaldehyde or chloral; ethylene glycol; diethylene glycol; thioglycol; a propane diol isomer; di- or tri-propylene glycol; glycerine, tri-methylol propane, hexane-1,6-diol or other isomer of hexane diol; hexahydroquinone; 1,4-bis-hydroxymethyl cyclohexane; terpin hydrate; mono-, di, tri- or tetra-methylol cyclohexanone; anhydroenneaheptiotol; phthalic or terephthalic acid diglycol ester; methylene glycol; a mono- or bis-hemiacetal of formaldehyde or chloral of any of the aforementioned polyhydroxyl compounds; n-methyl diethanolamine; bis hydroxyethyl cyclo-hexylamine; and bis-hydroxyethyl stearylamine, and an N-methylol derivative of valeorlactam, butyrolactam, caprolactam, propiolactam, N-butylethylurethan, N-methylol benzamide, N-hydroxymethyl naphthalimide, ethanolamine, N-methylethanol amine, cyclohexylethanolamine, oxethylated benzoic acid amide, hydroxyethyl acetamide, hydroxyethyl carbamic acid butyl ester, N,N-dimethylethanolamine, N,N-diethylethanolamine, and hydroazinoethanol, said adduct containing from 0.3 to 4 moles of said alcohol per mol of said lactam.

2. Adduct of a lactam selected from the group of epsilon-caprolactam, 1-N-methyl hexahydro-1,4-diazepin-3-one, propiolactam, butyrolactam, valerolactam and dodecalactam, with primary and secondary alcohols containing cyclic acetal group of formaldehyde, acetaldehyde or acrolein and alcohols with carbonyl or oxirane groups in the molecule, said adduct containing from 0.3 to 4 moles of said alcohol per mol of said lactam.

3. Adduct of claim 2 wherein the alcohol is selected from the group of

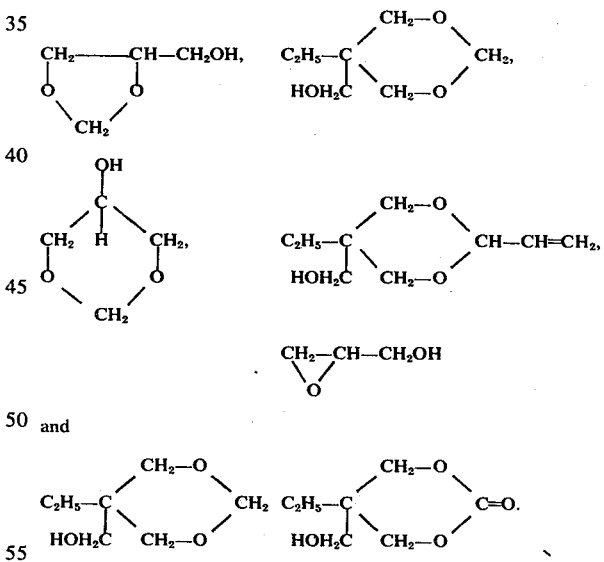

and

4. Process for the preparation of the adduct of claim 1 which comprises contacting said lactam with from 0.3 to 4 mols, per mol of lactam, of said alcohol at a temperature of from 20° to 150°C.

5. Process of claim 4 wherein the amount of alcohol used is from 1 to 3 mols per mol of lactam.

6. Process of claim 4 wherein the amount of alcohol used is from 1.2 to 2 mols per mol of lactam.

7. Process of claim 4 wherein the temperature is from 40° to 110°C.

8. Process of claim 4 wherein the temperature is from 50° to 80°C.

* * * * *

UNITED STATES PATENT OFFICE
CERTIFICATE OF CORRECTION

Patent No. 3,968,104            Dated    July 6, 1976

Inventor(s) Kuno Wagner

It is certified that error appears in the above-identified patent and that said Letters Patent are hereby corrected as shown below:

Col. 4, line 19, "hydroxymethyl" should read:
--hydroxyethyl --

Col. 4, Lactam Component No. 4, add bond between "C=O" and "(CH$_2$)$_3$-N"

Col. 5, line 27, add bond between "(CH$_2$)$_5$" and "N"

Col. 5, line 50, "compound" should read -- compounds --

Col. 5, line 51, "exmple" should read -- example --

Col. 5, line 55, "powder" should read -- power --

Col. 17, line 10, "shos" should read -- shows --.

Signed and Sealed this

Thirtieth Day of November 1976

[SEAL]

Attest:

RUTH C. MASON
Attesting Officer

C. MARSHALL DANN
Commissioner of Patents and Trademarks